United States Patent [19]

Krämer et al.

[11] Patent Number: 4,472,395
[45] Date of Patent: Sep. 18, 1984

[54] COMBATING FUNGI WITH NOVEL 2-AZOLYLMETHYL-1,3-DIOXOLANE AND -DIOXANE DERIVATIVES

[75] Inventors: Wolfgang Krämer, Wuppertal; Karl H. Büchel, Burscheid; Hans-Ludwig Elbe, Wuppertal; Udo Kraatz, Leverkusen; Wolf Reiser, Wuppertal; Andreas Schulze, Berg.-Gladbach; Erik Regel, Wuppertal; Wilhelm Brandes, Leichlingen; Paul-Ernest Frohberger, Leverkusen, all of Fed. Rep. of Germany

[73] Assignee: Bayer Aktiengesellschaft, Leverkusen, Fed. Rep. of Germany

[21] Appl. No.: 343,054

[22] Filed: Jan. 27, 1982

[30] Foreign Application Priority Data

Feb. 7, 1981 [DE] Fed. Rep. of Germany ....... 3104311

[51] Int. Cl.$^3$ .............. A01N 43/50; A01N 43/64; C07D 405/06; C07D 405/14
[52] U.S. Cl. .................. 424/245; 424/250; 424/269; 424/273 R; 424/232; 548/101; 548/262; 548/336; 544/366; 544/370
[58] Field of Search ............... 548/101, 262, 336; 544/366, 370; 424/245, 232, 269, 273 R, 250

[56] References Cited

U.S. PATENT DOCUMENTS

| | | | |
|---|---|---|---|
| 4,079,062 | 3/1978 | van Reet et al. | 548/262 |
| 4,156,008 | 5/1979 | Heeres | 424/273 R |
| 4,329,342 | 5/1982 | Heeres et al. | 424/245 |
| 4,375,474 | 3/1983 | Walker | 548/336 |
| 4,402,963 | 9/1983 | Sturm | 548/262 |

FOREIGN PATENT DOCUMENTS

| | | |
|---|---|---|
| 2804096 | 3/1978 | Fed. Rep. of Germany . |
| 2803870 | 8/1978 | Fed. Rep. of Germany . |
| 2943631 | 5/1980 | Fed. Rep. of Germany . |
| 2303475 | 10/1976 | France ................ 424/269 |

Primary Examiner—Alton D. Rollins
Attorney, Agent, or Firm—Sprung, Horn, Kramer & Woods

[57] ABSTRACT

A 2-azolylmethyl-1,3-dioxolane or -dioxane derivative of the formula

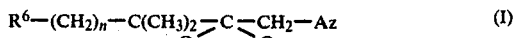

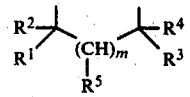

in which
Az is imidazol-1-yl or 1,2,4-triazol-1-yl,
$R^1$, $R^2$, $R^3$ and $R^5$ each independently is hydrogen or alkyl, or
$R^1$ and $R^3$ together are an optionally substituted multi-membered methylene bridge,
$R^4$ is hydrogen, optionally substituted alkyl, optionally substituted aryl or optionally substituted aralkyl,
m is 0 or 1,
$R^6$ is hydrogen, halogen, cyano, alkyl, optionally substituted aryl, —X—$R^7$, —COO$R^8$ or —CONH$R^9$,
X is oxygen, sulphur, SO, or $SO_2$,
$R^7$ is alkyl, halogenoalkyl, cyano, optionally substituted aralkyl or optionally substituted aryl,
$R^8$ is alkyl,
$R^9$ is alkyl or optionally substituted aryl, and
n is 0 or 1, or a plant-tolerated acid addition salt or metal salt complex thereof which possesses fungicidal activity.

13 Claims, No Drawings

COMBATING FUNGI WITH NOVEL 2-AZOLYLMETHYL-1,3-DIOXOLANE AND -DIOXANE DERIVATIVES

The present invention relates to certain new 2-azolylmethyl-1,3-dioxolane and -dioxane derivates, to a process for their preparation and to their use as fungicides.

It has already been disclosed that N-halogenoalkylmercapto-imides, such as N-trichloromethylthio-tetrahydrophthalimide, exhibit good fungicidal properties (see R. Wegler, Chemie der Pflanzenschutz-und Schädlingsbekämpfungsmittel (Chemistry of Plant Protection Agents and Pesticides), Volume 2, page 108 (1970)). Furthermore, it is already known that triazolylethyl benzyl ethers, such as [1-(2,4-dichlorophenyl)-2-(1,2,4-triazol-1-yl)-ethyl]-(2,6-dichlorobenzyl)-ether or -(3,4-dichlorobenzyl)-ether, possess a good fungicidal action (see U.S. application Ser. No. 43,070, filed May 29, 1979, now U.S. Pat. No. 4,400,388.

However, in certain fields of indication the action of all these compounds is not always entirely satisfactory, especially if small amounts and low concentrations are used.

The present invention now provides, as new compounds, the 2-azolylmethyl-1,3-dioxolane and -dioxane derivatives of the general formula

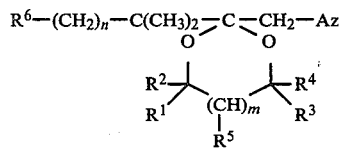

(I)

in which
Az represents imidazol-1-yl or 1,2,4-triazol-1-yl,
$R^1$ represents hydrogen or alkyl,
$R^2$ represents hydrogen or alkyl,
$R^3$ represents hydrogen or alkyl,
$R^4$ represents hydrogen, optionally substituted alkyl, optionally substituted aryl or optionally substituted aralkyl,
$R^1$ and $R^3$ can alternatively represent an optionally substituted multi-membered methylene bridge,
$R^5$ represents hydrogen or alkyl,
m represents 0 or 1,
$R^6$ represents hydrogen, halogen, cyano, alkyl, optionally substituted aryl or a grouping —X—$R^7$, —COO$R^8$ or —CONH$R^9$,
X represents oxygen, sulphur, the SO group or the SO$_2$ group,
$R^7$ represents alkyl, halogenoalkyl, cyano, optionally substituted aralkyl or optionally substituted aryl,
$R^8$ represents alkyl,
$R^9$ represents alkyl or optionally substituted aryl and
n represents 0 or 1, and their plant-tolerated acid addition salts and metal salt complexes.

The compounds of the formula (I) can, where relevant, occur as different stereoisomers; preferably, they are obtained in the form of stereoisomer mixtures.

The invention also provides a process for the preparation of a 2-azolyl-methyl-1,3-dioxolane or -dioxane derivative of the formula (I) in which (a) a substituted 1,3-dioxolane or dioxane derivative of the general formula

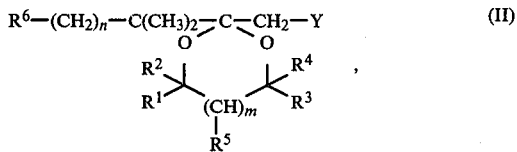

(II)

in which
$R^1$ to $R^6$, m and n have the abovementioned meanings, and
Y represents halogen, especially chlorine or bromine, or a grouping —O—SO$_2$—Z, wherein
Z represents methyl or p-methylphenyl, is reacted with an alkali metal salt of an azole of the general formula

M—Az    (III), in which
Az has the abovementioned meaning and
M represents an alkali metal, in the presence of a diluent, or (b) an azolylmethyl-keto derivative of the general formula

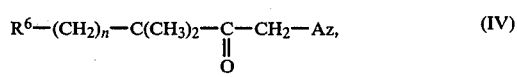

(IV)

in which
Az, $R^6$ and n have the abovementioned meanings, is reacted with a diol of the general formula

(V)

in which
$R^1$ to $R^5$ and m have the abovementioned meanings, in the presence of a diluent and in the presence of an acid as a catalyst.

The compounds of the formula (I), thus obtained, can, if desired, subsequently be subjected to an addition reaction with an acid or a metal salt. In come cases it proves advantageous to obtain the compounds of the formula (I) in a pure form via their salts.

The 2-azolylmethyl-1,3-dioxolane and -dioxane derivatives of the formula (I) exhibit powerful fungicidal properties. At the same time, the compounds according to the invention surprisingly show a better fungicidal action than the compounds N-trichloromethylthio-tetrahydrophthalimide and [1-(2,4-dichlorophenyl)-2-(1,2,4-triazol-1-yl)-ethyl]-(2,6-dichlorobenzyl)-ether or -(3,4-dichlorobenzyl)-ether, known from the prior art, which are compounds having a similar action. The compounds according to the invention thus represent an enrichment of the art.

Preferred compounds of the formula (I) are those in which
$R^1$ represents hydrogen or straight-chain or branched alkyl with 1 to 4 carbon atoms,
$R^2$ represents hydrogen or straight-chain or branched alkyl with 1 to 4 carbon atoms,
$R^3$ represents hydrogen or straight-chain or branched alkyl with 1 to 4 carbon atoms, $R^4$ represents hydrogen, or straight-chain or branched alkyl with 1 to 4 carbon atoms which can optionally be substituted by hydroxyl, alkoxy with 1 to 4 carbon atoms, dialkylamine or dialkylaminocarbonyl, each with 1 to 2 carbon atoms in each alkyl part, optionally substituted phenoxy, optionally substituted phenylalkoxy with 1 to 4 carbon atoms in the alkyl part, optionally substituted phenylcarbonyloxy, optionally substituted phenylalkylcarbonyloxy with 1 to 4 carbon atoms in the alkyl part, alkylsulphonyloxy with 1 to 4 carbon atoms or optionally substituted phenylsulphonyloxy, the substituent(s) on the phenyl moiety in each case preferably being selected from halogen, alkyl with 1 to 4 carbon atoms, alkoxy and alkylthio each with 1 to 2 carbon atoms, halogenoalkyl, halogenoalkoxy and halogenoalkylthio, each with 1 to 2 carbon atoms and 1 to 5 identical or different halogen atoms (especially fluorine and chlorine atoms), dimethylamino, acetylamino, acetyl-methylamino and optionally methyl-substituted or acetyl-substituted piperazinyl, or $R^4$ represents optionally substituted phenyl or optionally substituted phenylalkyl with 1 to 4 carbon atoms in the alkyl part, the substituent(s) on the phenyl in either case being preferably selected from halogen, alkyl with 1 to 4 carbon atoms, alkoxy and alkylthio each with 1 to 2 carbon atoms, halogenoalkyl, halogenoalkoxy and halogenoalkylthio, each with 1 to 2 carbon atoms and 1 to 5 identical or different halogen atoms (especially fluorine and chlorine atoms), dimethylamino, acetylamino, acetyl-methylamino and optionally methyl-substituted or acetyl-substituted piperazinyl, or $R^1$ and $R^3$ conjointly represent a tetramethylene or pentamethylene bridge which is optionally substituted by alkyl with 1 to 4 carbon atoms, $R^5$ represents hydrogen or straight-chain or branched alkyl with 1 to 4 carbon atoms;

$R^6$ represents hydrogen, halogen, cyano, straight-chain or branched alkyl with 1 to 4 carbon atoms or optionally substituted phenyl, the substituent(s) preferably being selected from halogen, alkyl with 1 to 4 carbon atoms, alkoxy and alkylthio each with 1 to 2 carbon atoms, halogenoalkyl, halogenoalkoxy and halogenoalkylthio, each with 1 to 2 carbon atoms and 1 to 5 identical or different halogen atoms (especially fluorine and chlorine atoms), dimethylamino, acetylamino, acetylmethylamino and optionally methyl-substituted or acetyl-substituted piperazinyl, or $R^6$ represents the grouping $-X-R^7$, $-COOR^8$ or $-CONHR^9$, $R^7$ represents straight-chain or branched alkyl with 1 to 4 carbon atoms, halogenoalkyl with 1 to 2 carbon atoms and 1 to 5 identical or different halogen atoms (especially fluorine and chlorine atoms), cyano, or optionally substituted phenyl or optionally substituted phenylalkyl with 1 to 4 carbon atoms in the alkyl part, the substituent(s) on the phenyl in either case preferably being selected from halogen, alkyl with 1 to 4 carbon atoms, alkoxy and alkylthio each with 1 to 2 carbon atoms, halogenoalkyl, halogenoalkoxy and halogenoalkylthio, each with 1 to 2 carbon atoms and 1 to 5 identical or different halogen atoms (especially fluorine and chlorine atoms), dimethylamino, acetylamino, acetyl-methylamino and optionally methyl-substituted or acetyl-substituted piperazinyl, $R^8$ represents straight-chain or branched alkyl with 1 to 4 carbon atoms, $R^9$ represents straight-chain or branched alkyl with 1 to 4 carbon atoms or optionally substituted phenyl, the substituent(s) preferably being selected from halogen, alkyl with 1 to 4 carbon atoms, alkoxy and alkylthio each with 1 to 2 carbon atoms, halogenoalkyl, halogenoalkoxy and halogenoalkylthio, each with 1 to 2 carbon atoms and 1 to 5 identical or different halogen atoms (especially fluorine and chlorine atoms), dimethylamino, acetylamino, acetyl-methylamino and optionally methyl-substituted or acetyl-substituted piperazinyl, n represents 1, and Az, X and m have the meanings given in the definition of the invention. Particularly preferred compounds of the formula (I) are those in which $R^1$, $R^2$ and $R^3$ have the preferred meanings, given above, $R^4$ represents hydrogen, or straight-chain or branched alkyl with 1 to 4 carbon atoms, which can optionally be substituted by hydroxyl, methoxy, ethoxy, dimethylamino, dimethylaminocarbonyl, optionally substituted phenoxy, optionally substituted benzyloxy, methylcarbonyloxy, ethylcarbonyloxy, optionally substituted phenylcarbonyloxy, optionally substituted benzylcarbonyloxy, methylsulphonyloxy, ethylsulphonyloxy or optionally substituted phenylsulphonyloxy, the substituent(s) on the phenyl moiety in each case being preferably selected from fluorine, chlorine, methyl, ethyl, methoxy, methylthio, trifluoromethyl, trifluoromethylthio, dimethylamino, acetylamino, acetyl-methylamino and 4-acetyl-piperazin-1-yl, or $R^4$ represents optionally substituted phenyl or optionally substituted benzyl, the substituent(s) on the phenyl preferably being selected, in either case, from fluorine, chlorine, methyl, ethyl, methoxy, methylthio, trifluoromethyl, trifluoromethylthio, dimethylamino, acetylamino, acetyl-methylamino and 4-acetyl-piperazin-1-yl, or $R^1$ and $R^3$ conjointly represent a tetramethylene bridge, $R^5$ represents hydrogen, methyl or ethyl, $R^6$ represents hydrogen, fluorine, chlorine, bromine, methyl, ethyl, propyl or optionally substituted phenyl, the substituent(s) preferably being selected from fluorine, chlorine, methyl, ethyl, methoxy, methylthio, trifluoromethyl, trifluoromethylthio, dimethylamino, acetylamino, acetyl-methylamino and 4-acetyl-piperazin-1-yl, or $R^6$ represents the grouping $-X-R^7$, $-COOR^8$ or $-CONHR^9$, $R^7$ represents methyl, ethyl, trifluoromethyl, cyano, optionally substituted phenyl or optionally substituted benzyl, the substituent(s) on the phenyl being in either case preferably selected from fluorine, chlorine, methyl, ethyl, methoxy, methylthio, trifluoromethyl, trifluoromethylthio, dimethylamino, acetylamino, acetyl-methylamino and 4-acetyl-piperazin-1-yl, $R^8$ represents methyl or ethyl, $R^9$ represents methyl, ethyl or optionally substituted phenyl, the substituent(s) preferably being selected from fluorine, chlorine, methyl, ethyl, methoxy, methylthio, trifluoromethyl, trifluoromethylthio, dimethylamino, acetylamino, acetyl-methylamino and 4-acetyl-piperazin-1-yl, n represents 1, and Az, X and m have the meanings given in the definition of the invention.

If, for example, 2-bromomethyl-2-[β-(4-chlorophenoxy)-α,α-dimethyl]-ethyl-4-ethyl-1,3-dioxolane and sodium-imidazole are used as starting materials in process variant (a), the course of the reaction can be represented by the following equation:

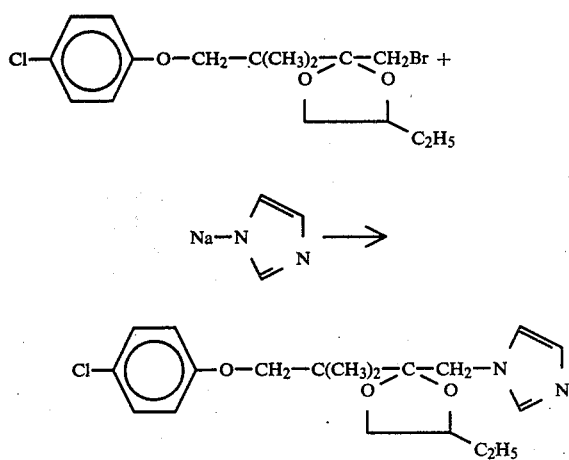

If, for example, 4-(4-chlorophenoxy)-3,3-dimethyl-1-(1,2,4-triazol-1-yl)-butan-2-one and 1,2-butanediol are used as starting materials in process variant (b), the course of the reaction can be represented by the following equation:

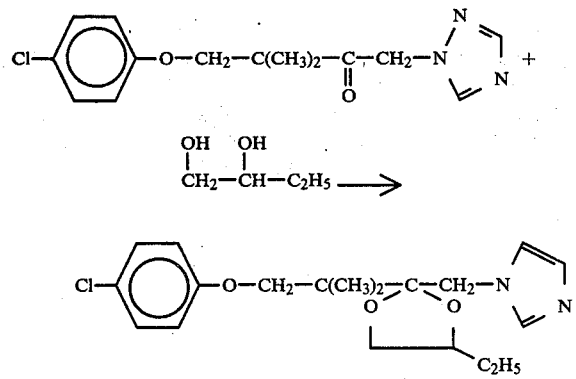

The formula (II) provides a general definition of the 2-halogenomethyl-1,3-dioxolane derivatives and -dioxane derivatives required as starting materials in carrying out process variant (a). In this formula, $R^1$, $R^2$, $R^3$, $R^4$, $R^5$, $R^6$ and the indices m and n preferably have the meanings which have already been mentioned as being preferred in the description of the compounds of the formula (I).

The substituted 1,3-dioxolane derivatives and dioxane derivatives of the formula (II) have not hitherto been described in the literature. They are obtained by reacting keto derivatives of the general formula

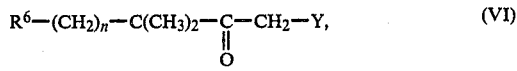

in which

Y, $R^6$ and n have the abovementioned meanings, with diols of the formula (V) in accordance with the conditions of process variant (b).

Keto derivatives of the formula (VI) are known (see U.S. application Ser. No. 819,533 filed July 27, 1977, now U.S. Pat. No. 4,331,674, and U.S. application Ser. No. 265,050 filed May 19, 1981, now U.S. Pat. No. 4,406,909 and U.S. application Ser. No. 328,871, filed Dec. 8, 1981. They are obtained, for example, by reacting the corresponding ketones with chlorine or bromine in the presence of an inert organic solvent, for example an ether or chlorinated or non-chlorinated hydrocarbon, at room temperature, or with a conventional chlorinating agent, for example sulphuryl chloride, at 20° to 60° C.

This formula (III) provides a general definition of the alkali metal salts of azoles which are also to be used as starting materials for process variant (a). In this formula, Az preferably has the meaning given in the general definition of the compounds of this invention. M preferably represents sodium or potassium.

Alkali metal salts of azoles of the formula (III) are generally known compounds. They are obtained by reacting imidazole or 1,2,4-triazole with sodium methylate or potassium methylate, or by reacting imidazole or triazole with the equivalent amount of the appropriate alkali metal hydride.

The formula (IV) provides a general definition of the azolylmethyl-keto derivatives to be used as starting materials in carrying out process variant (b). In this formula, Az, $R^6$ and the index n preferably have the meanings which have already been mentioned as being preferred in connection with the description of the compounds of the formula (I).

Some of the azolylmethyl-keto derivatives of the formula (IV) are known compounds (see, for example, U.S. application Ser. No. 291,700 filed Aug. 10, 1981 and U.S. application Ser. No. 291,699 filed Aug. 10, 1981, both now pending and U.S. application Ser. No. 112,811 filed Jan. 17, 1980, now pending and U.S. application Ser. No. 283,307 filed July 14, 1981, now pending and U.S. application Ser. No. 328,871 filed Dec. 8, 1981. They are obtained by reacting keto derivatives of the formula (VI) with alkali metal salts of azoles of the formula (III) under the conditions of process variant (a), or by reacting the derivatives of the formula (VI) directly with azoles in the customary manner, in the presence of an acid acceptor.

The formula (V) provides a general definition of the diols which are also to be used as starting materials for process variant (b). In this formula, $R^1$, $R^2$, $R^3$, $R^4$, $R^5$ and the index m preferably have the meanings which have already been mentioned as being preferred in connection with the description of the compounds of the formula (I).

The diols of the formula (V) are generally known compounds in organic chemistry, or are obtained in a generally known manner.

Suitable diluents for process variant (a) are inert organic solvents. These include, as preferences, amides, such as dimethylformamide or dimethylacetamide, dimethylsulphoxide and hexamethylphosphorotriamide.

In carrying out process variant (a), the reaction temperatures can be varied within a substantial range. In general, the reaction is carried out at between 20° and 150° C., preferably at from 60° to 150° C.

In carrying out process variant (a), preferably 1 to 2 mols of azole alkali metal salt of the formula (III) are employed per mol of compound of the formula (II). The resultant compound of the formula (I) may be isolated in the usual manner.

Suitable diluents for process variant (b) are inert organic solvents. These include aromatic hydrocarbons, such as benzene, toluene or xylene; halogenated aliphatic and aromatic hydrocarbons, such as carbon tetrachloride, chloroform, methylene chloride, chlorobenzene or dichlorobenzene; and mixtures of these solvents with alcohols, for example butanol. However, it is also possible, where desired, to use an appropriate excess of diol of the formula (V).

Process variant (b) is preferably carried out in the presence of a strong acid as the catalyst. Preferred strong acids are hydrochloric acid, hydrobromic acid, sulphuric acid and, in particular, p-toluene-sulphonic acid.

In carrying out process variant (b) the reaction temperatures can be varied within a substantial range. In general, the reaction is carried out at between 40° and 180° C., preferably at from 80° to 180° C. If appropriate, the reaction can also be carried out under elevated pressure.

In carrying out process variant (b), preferably 1 to 2 mols of diol of the formula (V) are used per mol of compound of the formula (IV), together with a catalytic amount of acid. The resultant compound of the formula (I) may be isolated in the usual manner.

To prepare physiologically tolerated acid-addition salts of the compounds of the formula (I), the following acids are preferably used: the hydrogen halide acids (for example hydrobromic acid and, especially, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and naphthalene-1,5-disulphonic acid). The acid addition salts of the compounds of the formula (I) can be obtained in a simple manner by customary salt-forming methods, for example by dissolving a compound of the formula (I) in a suitable inert solvent and adding the acid, for example hydrochloric acid, and can be isolated in a known manner, for example by filtering off, and can be purified, if necessary, by washing with an inert organic solvent.

To prepare metal salt complexes of the compounds of formula (I), salts of metals of main groups II to IV and of sub-groups I, II and IV to VIII are preferably used, and of these copper, zinc, manganese, magnesium, tin, iron and nickel may be mentioned as examples.

Preferred anions of the salts are those derived from the following acids: hydrogen halide acids (for example hydrochloric acid and hydrobromic acid), phosphoric acid, nitric acid and sulphuric acid.

The metal salt complexes of compounds of the formula (I) can be obtained in a simple manner by customary processes, for example by dissolving the metal salt in an alcohol, for example ethanol, and adding the solution to the compound of the formula (I). Metal salt complexes can be isolated in a known manner, for example by filtering off, and, where appropriate, can be purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Venturia species, such as against the apple scab causative organism (*Fusicladium dendriticum*), and for combating Uromyces and Puccinia species, such as against the bean rust causative organism (*Uromyces phaseoli*) and the cereal rust causative organism (*Puccinia recondita*), as well as for combating cereal diseases, such as against the powdery mildew of barley causative organism (*Erysiphe graminis*) and against the barley stripe disease causative organism (*Helminthosporium gramineum*). The compounds according to the invention also exhibit a good in-vitro action, especially against causative organisms of diseases of rice plants.

The partially systemic action of the compounds according to the invention is to be singled out. Thus, it proves possible to protect plants against fungal attack by supplying the active compound to the aerial parts of the plant via the soil and the root.

When used in appropriate amounts, the compounds according to the invention also exhibit growth-regulating properties.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to day liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such, or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably beween 0.5 and 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.0001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent. The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

(a) 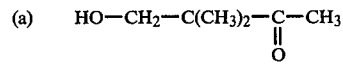

66 g (2.2 mols) of paraformaldehyde and 1 g of potassium hydroxide in 10 ml of methanol were added dropwise to 172 g (2 mols) of methyl isopropyl ketone in 1,000 ml of methanol. The mixture was heated under reflux for 15 hours and the methanol was then distilled off through a column, at 82° C. internal temperature. The residue was distilled in a waterpump vacuum. 152.7 g (68% of theory) of 2,2-dimethyl-1-hydroxy-butan-3-one of boiling point 80°–82° C./16 mbar, were obtained.

(b) 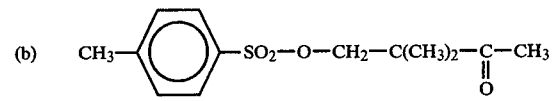

47.6 g (0.25 mol) of 4-toluenesulphonyl chloride were dissolved in 100 ml of chloroform, 35 g (0.3 mol) of 2,2-dimethyl-1-hydroxy-butan-3-one were added and 40 ml (0.5 mol) of pyridine were introduced dropwise at 0° to 5° C. The reaction mixture was then stirred for 15 hours at room temperature and was poured onto 200 g of ice and 70 ml of concentrated hydrochloric acid, and the organic phase was separated off, washed with three times 200 ml of water, dried over sodium sulphate and concentrated. The residue was taken up in 100 ml of petroleum ether, whereupon the end product crystallized out. 46 g (71% of theory) of 2,2-dimethyl-1-tosyloxy-butan-3-one were obtained as colorless crystals of melting point 49°–52° C.

(c) 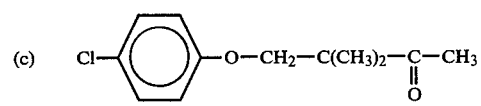

29.7 g (0.55 mol) of sodium methylate were dissolved in 500 ml of methanol and 70.4 g (0.55 mol) of 4-chlorophenol were added, with stirring. After 10 minutes' stirring, the solvent was distilled off under reduced pressure and the residue was taken up in 100 ml of glycol. This solution was added to a solution of 135 g (0.5 mol) of 2,2-dimethyl-1-tosyloxy-butan-3-one in 200 ml of glycol. The reaction mixture was stirred for 48 hours at 100° to 120° C. and was cooled and stirred into 2,000 ml of water. The mixture was extracted twice with 250 ml of diethyl ether and the combined organic phases were washed three times with 100 ml of water each time, once with 100 ml of 10% strength sodium hydroxide solution and again with 100 ml of water, dried over sodium sulphate and distilled.

62.9 g (55.7% of theory) of 1-(4-chlorophenoxy)-2,2-dimethyl-butan-3-one, of boiling point 135°-140° C./0.55 mbar, were obtained.

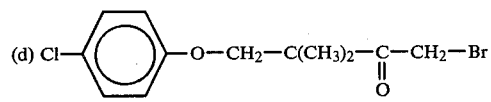

26 g (0.159 mol) of 1-(4-chlorophenoxy)-2,2-dimethyl-butan-3-one were dissolved in 300 ml of chloroform and 25.5 g (0.159 mol) of bromine were added dropwise, at 20° C. at such a rate that decoloration took place continuously. After completion of the addition, the mixture was stirred for 30 minutes at room temperature and was then concentrated by distilling off the solvent in vacuo. 48.5 g (quantitative conversion) of 1-bromo-4-(4-chlorophenoxy)-3,3-dimethylbutan-2-one of boiling point 150°-160° C./0.19 mbar, were obtained.

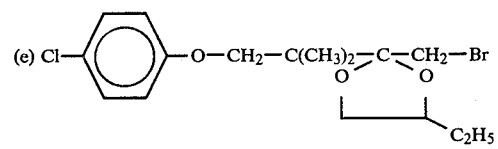

91 g ($3 \times 10^{-1}$ mol) of 1-bromo-3,3-dimethyl-4-(4-chlorophenoxy)-butan-2-one were dissolved in 400 ml of toluene, 54 g ($6 \times 10^{-1}$ mol) of 1,2-butanediol and 5.2 g ($3 \times 10^{-2}$ mol) of p-toluenesulphonic acid were added and the reaction mixture was then heated under reflux for 16 hours, using a water separator. After cooling, the organic phase was washed twice with 250 ml of saturated sodium bicarbonate solution and the solvent was distilled off in a waterpump vacuum. 120 g of crude 2-bromomethyl-2-[β-(4-chlorophenoxy)-α,α-dimethyl]-ethyl-4-1,3-dioxolane (62% content of pure product, determined by gas chromatography) were obtained, which product was further reacted direct.

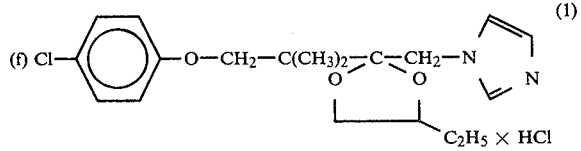

Process variant (a).

25.8 g ($3.8 \times 10^{-1}$ mol) of imidazole were dissolved in 600 ml of dimethylformamide, 20.5 g ($3.8 \times 10^{-1}$ mol) of sodium methylene, dissolved in 60 ml of methanol, were added dropwise, and the methanol was distilled off. 74 g ($1.9 \times 10^{-1}$ mol) of crude 2-bromomethyl-2-[β-(4-chlorophenoxy)-α,α-dimethyl]-ethyl-1,3-dioxolane (containing 62% of pure product) were added dropwise at 80° C. and heating was continued for 6 hours under reflux. After the mixture had cooled, it was stirred into 2 liters of water, the mixture was extracted twice with 500 ml of toluene, the combined toluene phases were extracted three times with 250 ml of water and the solvent was distilled off in a waterpump vacuum. The residue was taken up in 300 ml of diisopropyl ether and a saturated solution of hydrogen chloride in ether was added. The precipitate formed was filtered off. 39.7 g (84% of theory) of 2-(imidazol-1-yl)-methyl-2[β-(4-chlorophenoxy)-α,α-dimethyl]-ethyl-4-ethyl-1,3-dioxolane hydrochloride, of melting point 146°-47° C., were obtained.

EXAMPLE 2

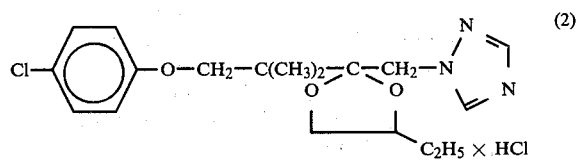

Process variant (a)

16.8 g ($3.1 \times 10^{-1}$ mol) of sodium methylate in 60 ml of methanol were added dropwise to 21.4 g ($3.1 \times 10^{-1}$ mol) of 1,2,4-triazole in 600 ml of dimethyl-formamide and the methanol was distilled off. 60 g ($1.56 \times 10^{-1}$ mol) of 2-bromomethyl-2-[β-(4-chlorophenoxy)-α,α-dimethyl]-ethyl-4-ethyl-dioxolane (62% content of pure product) were added at 80° C. and the reaction mixture was heated under reflux for 15 hours. The cooled dimethylformamide solution was stirred into 2 liters of water and the mixture was extracted with twice 250 ml of toluene. The toluene phase was washed with three times 250 ml of water and dried over sodium sulphate, and the solvent was distilled off in a waterpump vacuum. 20 g of crude product were obtained; this was taken up in 200 ml of diethyl ether and 20 ml of a saturated solution of hydrogen chloride in ether were added. The solvent was distilled off and the residue was again taken up in 200 ml of ether. An oil was obtained, from which the ether phase was decanted. After chromatography on a silica gel column (250 g of silica gel 60) in chloroform/methanol, 7.8 g (17.4% of theory) of 2-(1,2,4-triazol-1-yl)-methyl-2-[β-(4-chlorophenoxy)-α,α-dimethyl]-ethyl-4-ethyl-1,3-dioxolane-hydrochloride, of melting point 109° C., were obtained.

The following compounds of the general formula

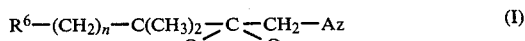

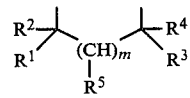

were obtained correspondingly and in accordance with the processes mentioned above.

| Compound No. | (structure with R¹-R⁵, (CH)ₘ) | R⁶ | n | Az | Melting point (°C.) |
|---|---|---|---|---|---|
| 3 | dioxolane with C₂H₅ | H | 1 | triazole (N-N=CH-N=CH) | 220 (× HCl) |
| 4 | dioxolane with C(CH₃)₃ | H | 1 | " | 132 (× HCl) |
| 5 | dioxolane with C₃H₇ | H | 1 | " | 190–92 (× HCl) |
| 6 | dioxolane with C₃H₇ | 4-Cl-C₆H₄-O- | 1 | " | 145 (× HCl) |
| 7 | dioxolane with C₂H₅ | 2,4-Cl₂-C₆H₃-O- | 1 | " | 156 (× HCl) |
| 8 | dioxolane with C₃H₇ | 2,4-Cl₂-C₆H₃-O- | 1 | " | 144 (× HCl) |
| 9 | dioxolane with C₂H₅ | 2,6-Cl₂-C₆H₃-O- | 1 | " | 138 (× HCl) |
| 10 | cyclohexane-fused dioxolane (H) | 2,4-Cl₂-C₆H₃-O- | 1 | " | 142 (× HCl) |
| 11 | dioxolane with C₂H₅ | 4-Br-C₆H₄-O- | 1 | " | 174 (× HCl) |
| 12 | dioxolane | 4-Cl-C₆H₄-O- | 1 | imidazole (-N-CH=CH-N=) | 169 (× HCl) |

-continued

| Compound No. | $R^1, R^2, R^3, R^4, R^5, (CH)_m$ structure | $R^6$ | n | Az | Melting point (°C.) |
|---|---|---|---|---|---|
| 13 | dioxolane with C₃H₇ | 4-Cl-C₆H₄-O— | 1 | " | viscous oil |
| 14 | dioxolane with CH₃ | 4-Cl-C₆H₄-O— | 1 | " | 127 (× HCl) |
| 15 | dioxolane with CH₂OH | 4-Cl-C₆H₄-O— | 1 | " | 148 (× HCl) |
| 16 | dioxolane with CH₃ | 2,4-Cl₂-C₆H₃-O— | 1 | " | 166 (× HCl) |
| 17 | dioxolane with C₂H₅ | 2,4-Cl₂-C₆H₃-O— | 1 | " | 158 (× HCl) |
| 18 | dioxolane with C₃H₇ | 2,4-Cl₂-C₆H₃-O— | 1 | " | 154 (× HCl) |
| 19 | dioxolane with C₂H₅ | 2,6-Cl₂-C₆H₃-O— | 1 | " | 169 (× HCl) |
| 20 | fused cyclohexane dioxolane (H) | 2,4-Cl₂-C₆H₃-O— | 1 | " | 135 (× HCl) |
| 21 | dioxolane with C₂H₅ | 4-Br-C₆H₄-O— | 1 | " | 176 (× HCl) |

-continued

| Compound No. | (structure with R¹-R⁵ as shown) | R⁶ | n | Az | Melting point (°C.) |
|---|---|---|---|---|---|
| 22 | dioxolane with C₃H₇ substituent | H | 1 | " | 173 (× HCl) |
| 23 | dioxolane with CH₂OH substituent | H | 1 | " | 168 (× HCl) |
| 24 | dioxolane fused with cyclohexane, H | H | 1 | " | 222 (× HCl) |
| 25 | dioxane with CH₃ substituent | 4-Cl-C₆H₄-O- | 1 | " | viscous oil |
| 26 | dioxane with CH₃ substituent | 4-Cl-C₆H₄-O- | 1 | " | 162 (× HCl) |
| 27 | dioxolane with C₂H₅ substituent | 4-Cl-C₆H₄-S- | 1 | " | 92 |
| 28 | dioxolane with C₂H₅ substituent | C₆H₅-S- | 1 | " | viscous oil |
| 29 | dioxolane with C₂H₅ substituent | C₆H₅-S- | 1 | 1,2,4-triazol-1-yl | viscous oil |
| 30 | dioxolane with CH₃ substituent | 4-Cl-C₆H₄-S- | 1 | " | viscous oil |
| 31 | dioxolane with CH₃ substituent | 4-Cl-C₆H₄-S- | 1 | imidazol-1-yl | viscous oil |

-continued

| Compound No. | R⁵ structure | R⁶ | n | Az | Melting point (°C.) |
|---|---|---|---|---|---|
| 32 | R⁵ = CH₃ | 2,4-dichlorophenoxy | 1 | -N(N=CH)N=CH- (triazole) | 152 (× HCl) |
| 33 | R⁵ = C₂H₅ | 2-chloro-5-methyl-phenoxy (H₃C, Cl, O-) | 1 | -N(CH=CH)N=CH- (imidazole) | 170 (× HCl) |
| 34 | R⁵ = CH₂—OSO₂CH₃ | 4-chlorophenoxy | 1 | triazole | crystal slurry |
| 35 | R⁵ = C₂H₅ | 3-methyl-4-chloro-phenoxy | 1 | " | 167 (× HCl) |
| 36 | R⁵ = C₂H₅ | 2-chloro-6-methyl-phenoxy | 1 | " | 129 (× HCl) |
| 37 | R⁵ = C₂H₅ | 2-chloro-6-methyl-phenoxy | 1 | imidazole | 184 (× HCl) |
| 38 | (no R⁵) | 4-chlorophenoxy | 1 | triazole | 180–82 (× HCl) |
| 39 | R⁵ = C₂H₅ | 4-methylphenoxy | 1 | " | $n_D^{20} = 1.5264$ |
| 40 | R⁵ = C₂H₅ | 2-methyl-4-bromo-phenoxy | 1 | " | $n_D^{20} = 1.5283$ |

-continued

| Compound No. | R⁵ (ring structure) | R⁶ | n | Az | Melting point (°C.) |
|---|---|---|---|---|---|
| 41 | dioxolane with C₂H₅ | 2-methyl-4-bromo-phenoxy | 1 | " | 137 (× ½ NDS)* |
| 42 | dioxolane with C₂H₅ | 4-chlorophenylthio | 1 | " | Oil |
| 43 | dioxolane with C₂H₅ | 4-chlorophenyl | 0 | " | 74 |
| 44 | dioxolane with two CH₃ | 2,4-dichlorophenoxy | 1 | " | 180 (× HCl) |
| 45 | dioxolane with two CH₃ | 2,4-dichlorophenoxy | 1 | imidazolyl | 160–168° C. (× HCl) |
| 46 | dioxolane (unsubstituted) | 2,4-dichlorophenoxy | 1 | " | 172° C. (× HCl) |
| 47 | dioxolane (unsubstituted) | 2,4-dichlorophenoxy | 1 | 1,2,4-triazolyl | 157–59° C. (× HCl) |
| 48 | dioxolane with C₂H₅ | 2-methyl-4-chloro-phenoxy | 1 | imidazolyl | 147–49° C. (× HCl) |
| 49 | dioxolane with C₂H₅ | 2-methyl-4-chloro-phenoxy | 1 | 1,2,4-triazolyl | 90° C. (× HCl) |

-continued $$\text{structure with } R^1, R^2, R^3, R^4, R^5, (CH)_m, O-C-O$$

| Compound No. | R⁵ (structure) | R⁶ | n | Az | Melting point (°C.) |
|---|---|---|---|---|---|
| 50 | dioxolane with -C₂H₅ | 4-Cl, 2-OCH₃, 5-CH₃ phenyl (CH₃, OCH₃, Cl substituted) | 1 | imidazole (-N⌒N) | 160° C. (× HCl) |
| 51 | dioxolane with -CH₂-O-(2,4-dichlorophenyl) | 4-Cl, phenyl-O- | 1 | " | 170° C. |
| 52 | dioxolane with -CH₂-N(C₂H₅)₂ | 4-Cl, phenyl-O- | 1 | " | half crystallized |
| 53 | dioxolane with -C₂H₅ | 4-Cl, 2-OCH₃, 5-CH₃ phenyl | 1 | triazole (-N-N⌒N) | 150° C. (× HCl) |
| 54 | dioxolane with -C₂H₅ | 2-CH₃, 4-NO₂, phenyl-O- (H₃C, O₂N, -O-) | 1 | " | 61° C. |
| 55 | dioxolane with -C₂H₅ | phenyl | 1 | imidazole | 102–4° C. |
| 56 | dioxolane with -C₃H₇ | H₃C-phenyl-O- | 1 | triazole | $n_D^{20} = 1.5419$ |
| 57 | dioxolane with -C₂H₅ | H₃C-, -O-, Br substituted phenyl | 1 | " | $n_D^{20} = 1.5080$ |
| 58 | dioxolane with -C₂H₅ | C₂H₅-, -O-, Br substituted phenyl | 1 | " | $n_D^{20} = 1.5252$ |

-continued

| Compound No. | R⁶ (structure with R¹-R⁵, (CH)m) | R⁶ | n | Az | Melting point (°C.) |
|---|---|---|---|---|---|
| 59 | O-C-O ring with C₂H₅ | 3,4-dimethyl-methoxyphenyl (H₃C, H₃C, —O—) | 1 | " | $n_D^{20} = 1.5368$ |
| 60 | O-C-O ring with C₂H₅ | 4-chlorophenyl | 1 | 1,2,4-triazolyl (–N linked to N=, N) | 138° C. |
| 61 | O-C-O ring | phenyl | 1 | " | 97° C. |
| 62 | O-C-O ring with C₂H₅ | 4-chlorophenyl | 1 | imidazolyl (–N, N) | 137° C. |
| 63 | O-C-O ring with C₂H₅ | 4-chlorophenoxy (Cl—⌬—O—) | 1 | imidazolyl | viscous Oil |
| 64 | O-C-O ring with C₃H₇ | 4-chlorophenoxy | 1 | " | 153–54 (× HCl) |
|  | O-C-O ring with —CH₂O—⌬—N(  )N—COCH₃ | 4-chlorophenoxy | 1 | " | viscous oil |
|  | O-C-O ring with C₃H₇ | 4-methylphenoxy (H₃C—⌬—O—) | 1 | " | $n_D^{20} = 1,5043$ |

*NDS = naphthalene-1,5-disulphonic acid

USE EXAMPLES

The fungicidal activity of the compounds of this invention is illustrated by the following examples wherein the compounds according to the present invention are each identified by the number (given in brackets) from the corresponding preparative example and table hereinabove;

The known comparison compounds are identified as follows:

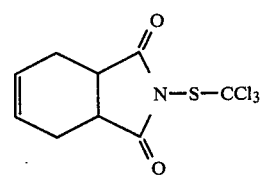

(A)

-continued (B)

[Structure: 3-Cl phenyl-CH(O-CH2-2,4-Cl2-phenyl)-CH2-N(triazole)]

(C)

[Structure: 4-Cl phenyl-CH(O-CH2-2,4-Cl2-phenyl)-CH2-N(triazole)]

EXAMPLE 3

Fusicladium test (apple)/protective
Solvent: 4.7 parts by weight of acetone
Emulsifier: 0.3 part of weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contained the stated addition.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (Fusicladium dendriticum) and incubated for 18 hours in a humidity chamber at 18° to 20° C. and at a relative atmospheric humidity of 100%.

The plants were then again brought into a greenhouse for 14 days.

15 days after inoculation, the infection of the seedlings was determined. The assessment data were converted to percent infection. 0% denoted no infection and 100% denoted that the plants were totally infected.

A distinct superiority in activity over the compound (A) known from the prior was shown in this test by, for example, the compounds (1), (2), (6), (7) and (8).

EXAMPLE 4

Uromyces test (beans)/protective
Solvent: 4.7 parts by weight of acetone
Emulsifier: 0.3 part by weight of alkylaryl polyglycol ether
Water: 95.0 parts by weight The amount of the active compound required for the desired concentration of the active compound in the spray liquid was mixed with the stated amount of solvent, and the concentrate was diluted with the stated amount of water which contained the stated additive.

Young bean plants in the 2-leaf state were sprayed with the spray liquid until dripping wet. The plants remained in a greenhouse for 24 hours at 20°-22° C. and a relative atmospheric humidity of 70% in order to dry. They were then inoculated with an aqueous uredospore suspension of the bean rust causative organism (Uromyces phaseoli) and incubated for 24 hours in a dark humidity chamber at 20°-22° C. and 100% relative atmospheric humidity.

The plants were then set up in a greenhouse under intensive illumination for 9 days at 20°-22° C. and a relative atmospheric humidity of 70-80%.

10 days after the inoculation, the infection of the plants was determined. The assessment data were converted to percent infection. 0% denoted no infection and 100% denoted that the plants were completely infected.

A distinct superiority in activity over the compounds (B) and (C) known from the prior art was shown in this test by, for example, the compounds (1), (2), (13), (25), (26), (16), (6), (7), (17), (18) and (8).

EXAMPLE 5

Puccinia Test (wheat)/protective
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were inoculated with a spore suspension of Puccinia recondita in a 0.1% strength aqueous agar solution. After the spore suspension had dried on, the plants were sprayed with the preparation of active compound until dew-moist. The plants remained in an incubation chamber at 20° C. and 100% relative atmospheric humidity for 24 hours.

The plants were placed in a greenhouse at a temperature of about 20° C. and a relative atmospheric humidity of about 80% in order to promote the development of rust pustules.

Evaluation was carried out 10 days after the inoculation.

A distinct superiority in activity over the compound (B) known from the prior art was shown in this test by, for example, the compounds (13), (6), (7), (17), (18), (8) and (19).

EXAMPLE 6

Powdery mildew of barley test (*Erysiphe graminis* var. *hordei*)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had unfolded their first leaf, they were dusted with fresh spores of *Erysiphe graminis* var. *hordei* and grown on at 21°-22° C. and 80-90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

A distinct superiority in activity over the compound (B) known from the prior art was shown in this test by, for example, the compounds (5) and (22).

EXAMPLE 7

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by Drechslera graminea (commonly described as Helminthosporium gramineum), was shaken with the dressing in a closed glass flask. The seed, on moist filter paper discs in closed petri dishes, was exposed to a temperature of 4° C. for 10 days in a refrigerator. The germination of the barley, and possibly also of the fungus spores, was thereby initiated. 2 batches of 50 grains of the pregerminated barley were subsequently sown 3 cm deep in Fruhstorfer standard soil and cultivated in a greenhouse at temperatures of about 18° C. in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

In this test, for example, a very good action, which was superior to the compound (B) known from the prior art, was shown by the compounds (5), (1), (12) and (13).

It will be appreciated that the instant specification and examples are set forth by way of illustration and not limitation, and that various modifications and changes may be made without departing from the spirit and scope of the present invention.

We claim:

1. A 2-azolylmethyl-1,3-dioxolane or -dioxane derivative of the formula

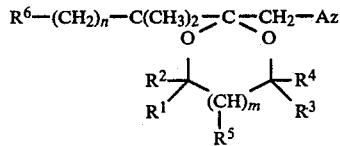

in which

Az is imidazol-1-yl or 1,2,4-triazol-1-yl, $R^1$ represents hydrogen or straight-chain or branched alkyl with 1 to 4 carbon atoms, $R^2$ represents hydrogen or straight-chain or branched alkyl with 1 to 4 carbon atoms, $R^3$ represents hydrogen or straight-chain or branched alkyl with 1 to 4 carbon atoms, $R^4$ represents hydrogen, or straight-chain or branched alkyl with 1 to 4 carbon atoms which can optionally be substituted by hydroxyl, alkoxy with 1 to 4 carbon atoms, dialkylamino or dialkylaminocarbonyl, each with 1 to 2 carbon atoms in each alkyl part, optionally substituted phenoxy, optionally substituted phenylalkoxy with 1 to 4 carbon atoms in the alkyl part, methylcarbonyloxy, ethylcarbonyloxy, optionally substituted phenylcarbonyloxy, optionally substituted phenylalkylcarbonyloxy with 1 to 4 carbon atoms in the alkyl part, alkylsulphonyloxy with 1 to 4 carbon atoms or optionally substituted phenylsulphonyloxy, the substituent(s) on the phenyl moiety in each case being selected from halogen, alkyl with 1 to 4 carbon atoms, alkoxy and alkylthio each with 1 to 2 carbon atoms, halogenoalkyl, halogenoalkoxy and halogenoalkylthio, each with 1 to 2 carbon atoms and 1 to 5 identical or different halogen atoms, dimethylamino, acetylamino, acetyl-methylamino and optionally methyl-substituted or acetyl-substituted piperazinyl, or $R^4$ represents optionally substituted phenyl or optionally substituted phenylalkyl with 1 to 4 carbon atoms in the alkyl part, the substituent(s) on the phenyl in either case being selected from halogen, alkyl with 1 to 4 carbon atoms, alkoxy and alkylthio each with 1 to 2 carbon atoms, halogenoalkyl, halogenoalkoxy and halogenoalkylthio, each with 1 to 2 carbon atoms and 1 to 5 identical or different halogen atoms, dimethylamino, acetylamino, acetylmethylamino and optionally methyl-substituted or acetyl-substituted piperazinyl, or $R^1$ and $R^3$ conjointly represent a tetramethylene or pentamethylene bridge which is optionally substituted by alkyl with 1 to 4 carbon atoms, $R^5$ represents hydrogen or straight-chain or branched alkyl with 1 to 4 carbon atoms, $R^6$ represents cyano, $-X-R^7$, $-COOR^8$ or $-CONHR^9$, X is oxygen, sulphur, SO or $SO_2$, $R^7$ represents optionally substituted phenyl or optionally substituted phenylalkyl with 1 to 4 carbon atoms in the alkyl part, the substituent(s) on the phenyl in either case being selected from halogen, alkyl with 1 to 4 carbon atoms, alkoxy and alkylthio each with 1 to 2 carbon atoms, $R^8$ represents straight-chain or branched alkyl with 1 to 4 carbon atoms, $R^9$ represents straight-chain or branched alkyl with 1 to 4 carbon atoms or optionally substituted phenyl, the substituent(s) being selected from halogen, alkyl with 1 to 4 carbon atoms, alkoxy and alkylthio each with 1 to 2 carbon atoms, halogenoalkyl, halogenoalkoxy and halogenoalkylthio, each with 1 to 2 carbon atoms and 1 to 5 identical or different halogen atoms, dimethylamino, acetylamino, acetyl-methylamino and optionally methyl-substituted or acetyl-substituted piperazinyl, m represents 0 or 1, and n represents 0 or 1, or a plant tolerated acid addition salt or metal salt complex thereof.

2. A compound salt or complex according to claim 1, in which $R^4$ represents hydrogen or straight-chain and branched alkyl with 1 to 4 carbon atoms, which can optionally be substituted by hydroxyl, methoxy, ethoxy, dimethylamino, dimethylaminocarbonyl, optionally substituted phenoxy, optionally substituted benzyloxy, methylcarbonyloxy, ethylcarbonyloxy, optionally substituted phenylcarbonyloxy, optionally substituted benzylcarbonyloxy, methylsulphonyloxy, ethylsulphonyloxy or optionally substituted phenylsulphonyloxy, the substituent(s) on the phenyl moiety in each case being selected from fluorine, chlorine, methyl, ethyl, methoxy, methylthio, trifluoromethyl, trifluoromethylthio, dimethylamino, acetylamino, acetyl-methylamino and 4-acetyl-piperazin-1-yl, or $R^4$ represents optionally substituted phenyl or optionally substituted benzyl, the substituent(s) on the phenyl in either case being selected from fluorine, chlorine, methyl, ethyl, methoxy, methylthio, trifluoromethyl, trifluoromethylthio, dimethylamino, acetylamino, acetyl-methylamino and 4-acetyl-piperazin-1-yl, or $R^1$ and $R^3$ conjointly represent a tetramethylene bridge, $R^5$ represents hydrogen, methyl or ethyl, $R^6$ represents the grouping —X—$R^7$, —COO$R^8$ and —CONH$R^9$, $R^7$ represents optionally substituted phenyl or optionally substituted benzyl, the substituent(s) on the phenyl being in either case selected from fluorine, chlorine, methyl, ethyl, methoxy and methylthio, $R^8$ represents methyl or ethyl, $R^9$ represents methyl, ethyl or optionally substituted phenyl, the substituent(s) being selected from fluorine, chlorine, methyl, ethyl, methoxy, methylthio, trifluoromethyl, trifluoromethylthio, dimethylamino, acetylamino, acetylmethylamino and 4-acetyl-piperazin-1-yl, and n represents 1.

3. A salt or complex according to claim 1, which is an addition salt of a hydrogen halide acid, phosphoric acid, nitric acid, sulphuric acid, a sulphonic acid or a mono- or di-carboxylic or hydroxycarboxylic acid, or in the form of a complex with a salt of which the metal is copper, zinc, manganese, magnesium, tin, iron or nickel and of which the anion is halide, sulphate, nitrate or phosphate.

4. A compound, salt or complex according to claim 1, in which $R^6$ is halophenoxy.

5. A complex, salt or addition product according to claim 4, in which
m is 0,
$R^1$, $R^2$ and $R^3$ are hydrogen, and
$R^4$ is not hydrogen.

6. A compound according to claim 1, wherein such compound is 2-(imidazol-1-yl)-methyl-2[β-(4-chlorophenoxy)-α,α-dimethyl]-ethyl-4-ethyl-1,3-dioxolane of the formula

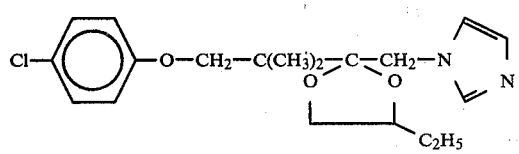

or a plant-tolerated acid addition salt or metal salt complex thereof.

7. A compound according to claim 1, wherein such compound is 2-(1,2,4-triazol-1-yl)-methyl-2-[β-(4-chlorophenoxy)-α,α-dimethyl]-ethyl-4- ethyl-1,3-dioxolane of the formula

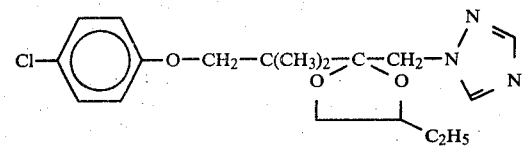

or a plant-tolerated acid addition salt or metal salt complex thereof.

8. A compound according to claim 1, wherein such compound is 2-(1,2,4-triazol-1-yl)-methyl-2-[β-(4-chlorophenoxy)-α,α-dimethyl]-ethyl-4-propyl-1,3-dioxolane of the formula

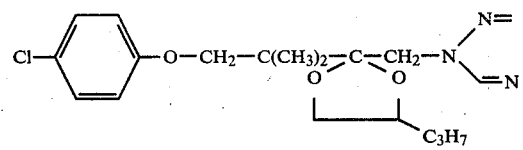

or a plant-tolerated acid addition salt or metal salt complex thereof.

9. A compound according to claim 1, wherein such compound is 2-(1,2,4-triazol-1-yl)-methyl-2-[β-(2,4-dichlorophenoxy)-α,α-dimethyl]-ethyl-4-ethyl-1,3-dioxolane of the formula

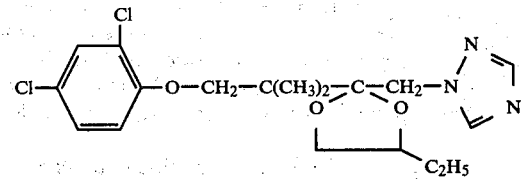

or a plant-tolerated acid addition salt or metal salt complex thereof.

10. A compound according to claim 1, wherein such compound is 2-(1,2,4-triazol-1-yl)-methyl-2-[β-(2,4-dichlorophenoxy)-α,α-dimethyl]-ethyl-4-propyl-1,3-dioxolane of the formula

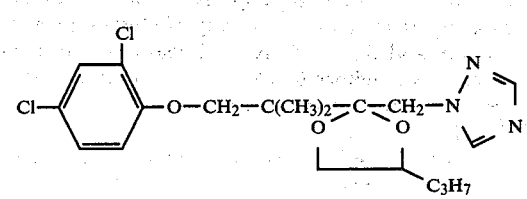

or a plant-tolerated acid addition salt or metal salt complex thereof.

11. A fungicidal composition comprising a fungicidally effective amount of a compound, salt or complex according to claim 1 in admixture with a diluent.

12. A method of combating fungi comprising applying to the fungi, or to a habitat thereof, a fungicidally effective amount of a compound, salt or complex according to claim 1.

13. The method according to claim 12, wherein such compound is
2-(imidazol-1-yl)-methyl-2[β-4-chlorophenoxy)-α,α-dimethyl]-ethyl-4-ethyl-1,3-dioxolane,
2-(1,2,4-triazol-1-yl)-methyl-2-[β-(4-chlorophenoxy)-α,α-dimethyl]-ethyl-4-ethyl-1,3-dioxolane, 2-(1,2,4-triazol-1-yl)-methyl-2-[β-(4-chlorophenoxy)-α,α-dimethyl]ethyl-4-propyl-1,3-dioxolane, 2-(1,2,4-triazol-1-yl)-methyl-2-[β-(2,4-dichlorophenoxy)-α,α-dimethyl]-ethyl-4-ethyl-1,3-dioxolane, or 2-(1,2,4-triazol-1-yl)-methyl-2-[β-(2,4-dichlorophenoxy)-α,α-dimethyl]-ethyl-4-propyl-1,3-dioxolane, or a plant-tolerated acid addition salt or metal salt complex thereof.

* * * * *

UNITED STATES PATENT AND TRADEMARK OFFICE
CERTIFICATE OF CORRECTION

PATENT NO. : 4,472,395           Page 1 of 2
DATED : September 18, 1984
INVENTOR(S) : Wolfgang Krämer, et al It is certified that error appears in the above-identified patent and that said Letters Patent is hereby corrected as shown below:

On the title page,
Under "Inventors", line 7 — Delete "Paul-Ernest" and substitute --Paul-Ernst--

Under "Foreign Patent Documents", line 1 — Delete "3/1978" and substitute --8/1978--

Abstract, line 13, Col. 1, line 48, Col. 2, line 10, Col. 2, line 42, Col. 4, line 17, Col. 5, line 6, Col. 5, line 60, Col. 6, line 58, Col. 30, line 58, and Col. 31, line 47 — Delete "m" and substitute --$\underline{m}$--

Abstract, line 22, Col. 1, line 59, Col. 2, line 10, Col. 2, line 32, Col. 4, line 16, Col. 5, line 5, Col. 5, line 60, Col. 6, line 7, Col. 6, line 37, Col. 30, line 59 and Col. 31, line 34 — Delete "n" and substitute --$\underline{n}$--

Col. 5, line 50 — Delete end of formula and substitute

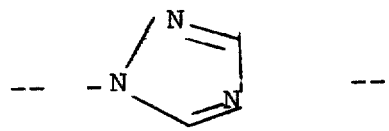

UNITED STATES PATENT AND TRADEMARK OFFICE
CERTIFICATE OF CORRECTION

PATENT NO. : 4,472,395

DATED : September 18, 1984

INVENTOR(S) : Wolfgang Krämer, et al

It is certified that error appears in the above-identified patent and that said Letters Patent is hereby corrected as shown below:

| | |
|---|---|
| Col. 11, line 52 | After "4-" insert --ethyl-- |
| Col. 27, line 29 | After "part" delete "of" and substitute --by-- |
| Col. 27, line 66 | Delete "state" and substitute --stage-- |

Signed and Sealed this

Twelfth Day of March 1985

[SEAL]

Attest:

DONALD J. QUIGG

Attesting Officer     Acting Commissioner of Patents and Trademarks